United States Patent [19]

Pracht

[11] Patent Number: 5,109,608
[45] Date of Patent: May 5, 1992

[54] SCISSORS, IN PARTICULAR HAIRDRESSER'S SCISSORS

[76] Inventor: Gunther Pracht, Nettelbeckstr. 17, Solingen, Fed. Rep. of Germany, D-5650

[21] Appl. No.: 585,166
[22] PCT Filed: Mar. 11, 1989
[86] PCT No.: PCT/EP89/00254
    § 371 Date: Oct. 15, 1990
    § 102(e) Date: Oct. 15, 1990
[87] PCT Pub. No.: WO89/10244
    PCT Pub. Date: Nov. 2, 1989

[30] Foreign Application Priority Data

Apr. 20, 1988 [DE] Fed. Rep. of Germany ....... 3813273

[51] Int. Cl.⁵ ............................................ B26B 13/12
[52] U.S. Cl. ......................................... 30/341; 30/232; 30/254
[58] Field of Search ................. 30/232, 231, 254, 298, 30/341, 235, 291

[56] References Cited

U.S. PATENT DOCUMENTS

| 927,058 | 7/1909 | Krouse | 30/341 |
| 4,254,551 | 3/1981 | Megna et al. | 30/341 |
| 4,642,895 | 2/1987 | Gauvry | 30/341 |
| 4,742,617 | 5/1988 | Gauvry | 30/232 |

FOREIGN PATENT DOCUMENTS

| 8604659 | 2/1986 | Fed. Rep. of Germany . |
| 8703303 | 5/1987 | Fed. Rep. of Germany . |
| 8801248 | 5/1988 | Fed. Rep. of Germany ........ 30/232 |

Primary Examiner—Douglas D. Watts
Assistant Examiner—Clark F. Dexter
Attorney, Agent, or Firm—Diller, Ramik & Wight

[57] ABSTRACT

Scissors, in particular hairdresser's scissors, in which the finger loop for the thumb is pivotable in a limited manner is simplified and improved under maintenance of the conventional shape in that the movable finger loop is mounted on at least one pin the axis of which extends obliquely relative to the center line of the scissors. The finger loop may preferably be mounted on two pins.

In order to be able to take the finger loop more easily with the thumb, the pivoting angle is limited to about 50°, i.e. the most advantageous region in ergonomic aspects, in that a finger loop having a broader wall is mounted in a handle ring on two pins, or the finger loop is mounted at the shorter handle on a pin and at the finger loop there is provided a projection which abuts the edge of the handle. Instead thereof, there may be provided a projection at the handle. on the one hand, and at the finger loop adjacent to the pin, on the other hand, in such a manner that the pivoting angle of the finger loop is limited to 50°.

12 Claims, 2 Drawing Sheets

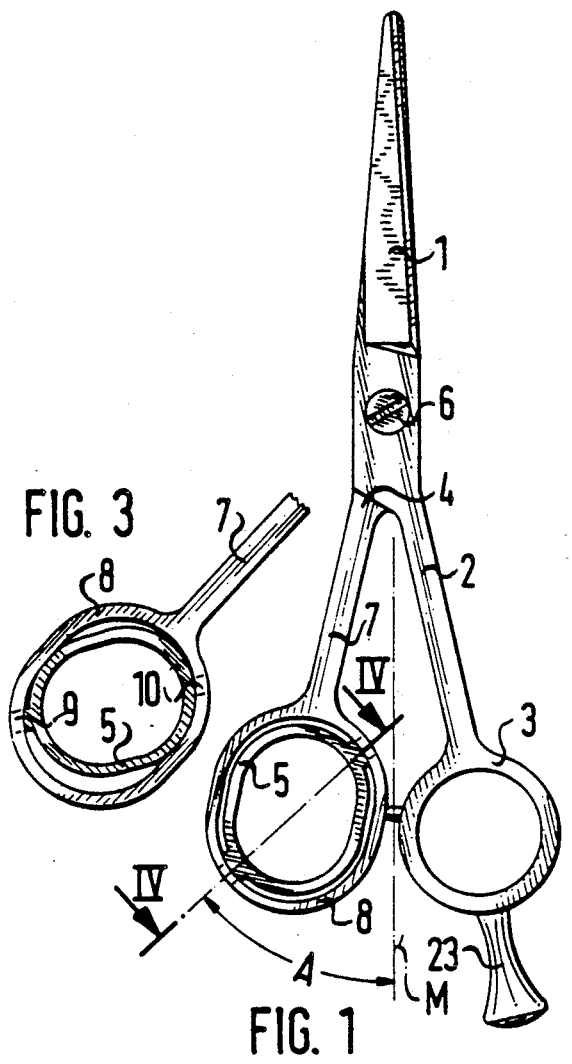
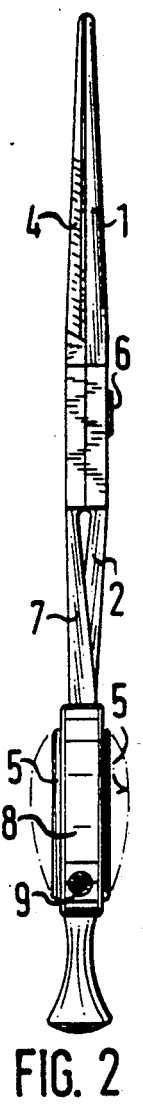
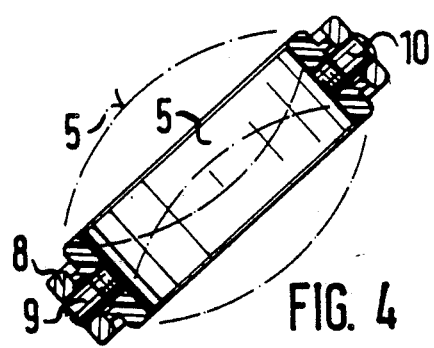

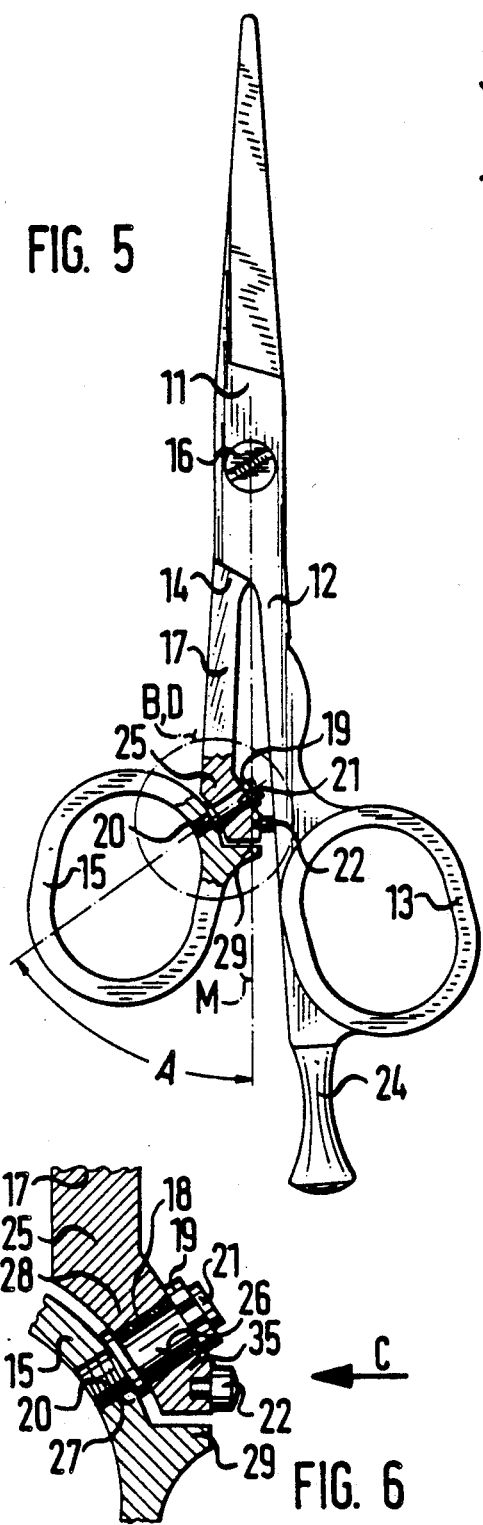
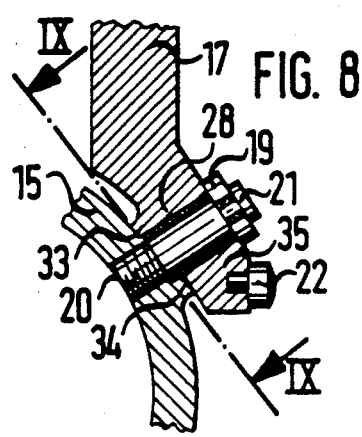
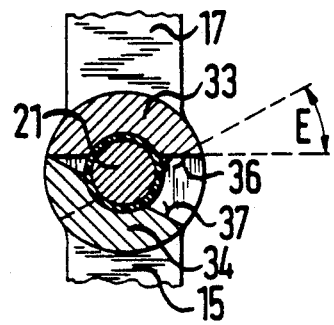
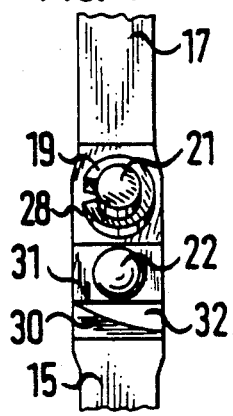

SCISSORS, IN PARTICULAR HAIRDRESSER'S SCISSORS

The invention relates to scissors, in particular hairdresser's scissors, with a longer handle, a finger loop as well as a shorter handle and a pivotable finger loop, wherein the pivotable finger loop is pivotably mounted in an axis, which extends obliquely relative to the centre line of the scissors.

Such scissors are known. They have the advantage as compared with scissors in which the finger loop of the movable scissor half is fixedly arranged that the finger loop fully engages the thumb with its inner surface, when the thumb is pushed therethrough and remains in this position during operation of the scissors. This has as a result that even in the case of longer and extended use of the scissors, no pressure marks will be produced at the thumb and stresses of the wrist will be avoided.

Scissors of the type named above are known from German patent No. 8801248.

In the case of such scissors, the thumb finger loop at the shorter handle as well as the finger loop at the longer handle exhibit a bolt which is pivotably mounted in a bore of a bushing provided for at the end of the corresponding handle in a rectangular position to the longitudinal axis of the handle.

Herewith the finger loops are pivotable with regard to an axis extending approximately in the plane of the scissors and approximately rectangular relative to the longitudinal axis of the scissors.

In order to achieve an ergonomically favorable handling of the scissors at various positions of use, the finger loops of the scissors are also limitedly tiltable with regard to an axis extending also in the plane of the scissors, however approximately parallel to the longitudinal axis of the scissors.

Due to the bushings for the rotary connection and the additional tiltable connection provided for at the ends of the handles, the mounting of the finger loops at the handles is relatively expensive with regard to the technical production. In addition, the scissors noticeably deviate from conventional shapes of hairdresser's scissors and look plump because of the bushings positioned at the ends of the handles normal to the longitudinal axis of the scissors and the finger loops directed outwardly and mounted in these bushings. Therefore a considerable number of hairdressers do not use these scissors in spite of their ergonomical advantages. In addition, the plump shape causes the hairdresser's to assume that the scissors are relatively heavy by weight and that therefore their handling is impaired. For this reason the hairdresser prefers conventional scissors, which however do not exhibit the ergonomical advantages.

Scissors of the type named above are also known from, U.S. Pat. No. 4,742,617. In the case of these scissors the thumb finger loop at the shorter handle is mounted at the shorter handle by a flexible connection member, which engages through an opening at the end of the handle by a flexible pin and through an opening at the finger loop by a flexible pin in such a way that its central axis forms an angle between 30° C. and 60° C. with the longitudinal axis of the scissors in the plane of the scissors and perpendicular to the plane of the scissors also at an angle between 30° and 60°. In these planes the finger loop is pivotable in a limited manner. The disadvantages mentioned above also apply to these scissors published subsequently.

It is the object of the invention to simplify and to improve the mounting of the movable finger loop destined for receiving the thumb and provided at the movable scissor half of the scissors of the kind mentioned at the beginning, namely under a large maintenance of the conventional shape of hairdresser's scissors.

A solution to this object is to mount at the shorter handle a handle ring with two pins, mounted inside, which are positioned in an axis arranged obliquely relative to the centre line of the scissors and which engage in bores of the pivotable finger loop.

The simple manner of arrangement of the movable finger loop in the handle ring allows production of the scissor halves with the handle rings in one piece, whereby advantageously the shape of conventional hairdresser's scissors is maintained.

In order to limit the angular region through which the movable finger loop may be pivoted, the wall of the movable finger loop is made broader than the wall of the handle ring.

As a result the movable finger loop abuts at the inner wall of the handle ring at the end of the pivoting motion.

Another solution to the object identified above, consists in arranging a bore in a bent portion directed to the longer handle, approximately at the end of the shorter handle and extending under an angle of 30° to 60° obliquely to the centre line of the scissors.

A pin fastened at the pivotable finger loop is inserted into the bore, being secured against unintentional loosening by means of a spring washer.

In this case, a handle ring at the movable scissor half is not required, since in accordance with the above-named known scissors, the pivotable finger loop is mounted at the handle.

As a consequence of the bent portion at the end of the shorter handle, which is directed to the longer handle and in which the finger loop is pivotable relative to a bore which extends under an angle of 30° to 60° obliquely to the centre line of the scissors, the pivotable finger loop is also arranged in a position which corresponds to conventional shapes of hairdresser's scissors.

Furthermore by loosening the spring washer, the pivotable finger loop can be exchanged for an adaption to a larger or smaller thumb.

The angle of the axis, around which the finger loop at the shorter handle is arranged, amounts in a preferred embodiment to 53°. On the contrary the angle between the centre line of the shorter handle and the axis, around which the pivotable finger loop is arranged, is substantially smaller in dependency of the spreading of the handle and amounts to 5° to 30°. The angle increases when the spreading of the handles decreases.

The pivotable finger loop destined for the thumb should not be totally freely pivotable about the pivoting axis, so that the scissors can be taken up by the user, in particular the hairdresser, easily with one hand when, for example, a comb is held with the other hand. The limitation of the pivoting angle can be obtained by simple means in that a projection with an inclined edge is arranged at the finger loop and a straight edge is arranged at the end of the bent portion of the handle in such a manner that after pivoting the finger loop by about 50°, the edge of the projection engages the other edge of the handle.

Another possibility for limiting the pivoting angle consists in arranging a projection with an inclined edge at the finger loop adjacent to the pin and in arranging a projection with an edge at the bent portion of the handle in such a way that after pivoting the finger loop by approximately 50°, the edge of the projection at the finger loop engages at the edge of the projection at the bent portion of the handle.

This design of the projections may be produced in a simple manner by, for example, milling the opposite faces at the finger loop and at the end of the shorter handle.

In scissors designed according to the invention, in particular hairdresser's scissors, in which, in a bent portion approximately at the end of the shorter handle, there is arranged a bore extending under an angle of 30° to 60° relative to the centre line of the scissors, into which bore a pin fastened to the pivotable finger loop is inserted and secured against unintentional loosening by means of, e.g. a spring washer, advantageously a projection having an inclined edge is arranged at the finger loop, and at the end of the bent portion of the handle there is arranged an approximately straight edge in such a manner that after pivoting the finger loop by about 50° the edge of the projection engages the other edge of the handle. In another advantageous embodiment for limiting the pivoting angle of the movable finger loop to an ergonomically advantageous pivoting region of 0° to about 50°, the finger loop has, adjacent to the pin and opposite to the end of the bent portions, a projection and, on the other hand, the handle has, on the side of the bent portion facing the finger loop, likewise a projection, these projections being provided at their sides facing one another and the pin with approximately straight edges in such a manner that they allow a pivoting angle of about 50°. The projections may be produced in a simple manner by, for example, milling the opposite faces at the finger loop and at the end of the shorter handle.

The details mentioned above as well as further details of the invention are explained below more exactly by means of the drawings. Therein is:

FIG. 1 a front elevational view of close hairdresser's scissors,

FIG. 2 a side elevational view of the scissors of FIG. 1,

FIG. 3 the handle ring with the movable finger loop with opened hairdresser's scissors in that position as if a thumb is pushed therethrough, FIG. 4 a sectional view, on an enlarged scale, on the line IV—IV of FIG. 1, FIG. 5 a simplified embodiment of hairdresser's scissors similar to FIG. 1 but without handle ring, FIG. 6 the detail "B" of FIG. 5 on an enlarged scale, FIG. 7 the detail "B" viewed in the direction of arrow "C" in FIG. 6.

FIG. 8 the detail "D" of FIG. 5, on an enlarged scale, which has been modified over the representation of FIG. 6, and FIG. 9 a sectional view on the line IX—IX of FIG. 8.

The hairdresser's scissors shown in FIGS. 1 to 4 consists of the scissor half 1 which is stationary during use of the scissors and has a handle 2 provided with the finger loop 3 having a finger support 23, and of the movable scissor half 4 having a pivotable finger loop 5. The scissor halves 1, 4 are connected by means of a joint screw 6. At the handle 7 of the movable scissor half 4 there is provided a handle ring 8 which is integral with the handle 7 and in which the pivotable finger loop 5 is mounted. The finger loop 5 is mounted on two pins 9, 10 which are firmly mounted to the inner wall of the handle ring 8 at both sides of the longitudinal axis thereof and which have an oblique position relative to one another in such a manner that the finger loop 5 fully engages the thumb with its inner face when opening the hairdresser's scissors after having pushed the thumb through the finger loop. The wall of the finger loop 5 is somewhat broader than the wall of the handle ring 8 (FIGS. 2 and 4) in order to limit the pivotability thereof.

The hairdresser's scissors shown in FIGS. 5 to 7 consists of the scissor half 11 which is stationary during use of the scissors and has a handle 12 provided with a finger loop 13 having a finger support 24, and of the scissor half 14 which is movable by means of the thumb and possesses a pivotable finger loop 15. The scissor halves are connected by means of a joint screw 16. At its end 25, the handle 17 of the movable scissor half 14 has a bent portion 28 directed towards the other scissor half 11, the bent portion 28 being provided with a bore 26 for a pin 21 (FIG. 6). The end 20 of the pin is firmly screwed into a threaded bore 27 of the finger loop 15. The pin 21 extends relative to the centre line M of the scissors at an angle A which may be between 30° to 60° and preferably amounts to 53°. After screwing the pin 21 into the threaded bore 27 of the finger loop 15, a sleeve 18 of plastic material is pushed onto the outer surface of the pin 21, and after the insertion into the bore 26, the pin 21 is secured against unintended loosening at the end 25 of the handle 17 by means of a spring washer 19. At the bent portion 28, towards the handle 12, there is arranged a resilient bumper 22 which prevents the metallic striking together of the handles 12 and 17. Between the edge 30 of a projection 29 provided at the finger loop 15 and the edge 31 of the bent portion 28, there is provided an angularly shaped space 32. When the scissors are pivoted during use out of the neutral position shown in FIG. 7, the finger loop 15 may be pivoted on the pin 21 until an abutment of the edges 30 and 31 occurs within a pivoting region of 5° to 50°. This is that region which is most favourable in ergonomic aspects. The limitation of the pivot angle facilitates the gripping of the scissors, in particular the finger loop 15 with the thumb of the user, since an oblique position of the finger loop 15 in a pivoting region which cannot be reached by the thumb is avoided.

A further advantageous embodiment for the limitation of the pivoting angle of the movable finger loop 15 in the pivoting region of 0° to about 50° is one in which, according to FIGS. 8 and 9, the finger loop 15 is provided with a projection 34 adjacent to the pin 21 and opposite to the end 35 of the bent portion 28, and the handle 17 is provided with a projection 33 at that side of the bent portion 28 which faces the finger loop 15. The projections 33 and 34 are provided, at their sides facing the pin 21, with approximately straight edges 36 and 37 in such a manner that they allow a pivoting angle E of about 50° between the finger loop 15 and the handle 17. These straight edges 36, 37 may be produced in a simple manner, e.g. by milling.

I claim:

1. Scissors, in particular hairdresser's scissors, comprising a long handle having a finger loop and a short handle having a pivotable finger loop, said pivotable finger loop being pivotably arranged about only one fixed oblique axis relative to a centre line of the scissors, a handle ring (8) being mounted on the short handle (7), and the short handle ring (8) having two pins (9, 10) mounted inside said short handle ring (8) which are arranged on said only one fixed axis oblique relative to a centre line (M) of the scissors and which engage in bores in the pivotable finger loop (5).

2. Scissors as claimed in claim 1, characterized in that, a wall of the pivotable finger loop (5) is broader than a wall of the handle ring (8).

3. Scissors as claimed in claim 2, characterized in that the pivotable finger loop (5, 15) of the short handle (7, 17) is pivotably mounted on said only one fixed axis extending obliquely at an angle in the range of 30° to 60° relative to a centre line (M) of the scissors.

4. Scissors as claimed in claim 1, characterized in that the pivotable finger loop (5) at the short handle (7) is pivotably mounted on said only one fixed axis extending obliquely at an angle in the range of 30° to 60° relative to a centre line (M) of the scissors.

5. Scissors as claimed in claim 1 wherein said only one fixed oblique axis and said centre line lie in a single plane, and means for pivoting said handles for relative movement in directions parallel to said single plane.

6. Scissors, in particular hairdresser's scissors, comprising a long handle having a finger loop and a short handle having a pivotable finger loop wherein the pivotable finger loop is pivotably arranged about only one oblique axis relative to the centre line of the scissors, approximately at an end (25) of the short handle (17) in a bent portion (28) which is directed towards the longer handle (12) there is arranged a bore (26), said bore (26) extending obliquely at said only one fixed angle in the range of 30° to 60° relative to a centre line (M) of the scissors, a pin (21) fastened to the pivotable finger loop (15), and said pin (21) being secured against unintentional loosening by means of a spring washer (19).

7. Scissors as claimed in claim 6, characterized in that a projection (29) having an inclined edge (30) is arranged at said pivotable finger loop (15) and that at an end (35) of the bent portion (28) of the short handle (17) there is arranged a straight edge (31) such that after pivoting the finger loop (15) by about 50° the edge (30) of the projection (29) engages another edge (31) of the handle (17).

8. Scissors as claimed in claim 6, characterized in that at said pivotable finger loop (15) (21) there is arranged a projection (34) adjacent to the pin, said projection having an inclined edge (37) and at the bent portion (28) of the short handle (17) there is arranged a projection (33) having an edge (36) such that after pivoting the finger loop (15) substantially 50° the inclined edge (37) of the projection (34) abuts the edge (36) of the projection (33).

9. Scissors as claimed in claim 6, characterized in that the pivotable finger loop (15) of the short handle (17) is pivotably mounted on said only one fixed axis extending obliquely at an angle in the range of 30° to 60° relative to the centre line (M) of the scissors.

10. Scissors as claimed in claim 9, characterized in that a projection (29) having an inclined edge (30) is arranged at the pivotal finger loop (15) and that at an end (35) of the bent portion (28) of the short handle (17) there is arranged a straight edge (31) such that after pivoting the pivotal finger loop (15) by about 50° the inclined edge (30) of the projection (29) engages the straight edge (31) of the short handle (17).

11. Scissors as claimed in claim 9, characterized in that at the pivotable finger loop (15) adjacent to a pin (21) there is arranged a projection (34) having an inclined edge (37) and at a bent portion (28) of the short handle (17) there is arranged a projection (33) having an edge (36) such that after pivoting the finger loop (15) substantially 50° the inclined edge (37) of the projection (34) abuts the edge (36) of the projection (33).

12. Scissors as claimed in claim 6 wherein said only one fixed oblique axis and said centre line lie in a single plane, and means for pivoting said handles for relative movement in directions parallel to said single plane.

* * * * *